(12) United States Patent
Terauchi

(10) Patent No.: US 7,080,981 B2
(45) Date of Patent: Jul. 25, 2006

(54) DEVICE FOR REMOVING A BROKEN INSTRUMENT, ASSISTING INSTRUMENTS, AND THE METHOD TO RETRIEVE A BROKEN INSTRUMENT FROM THE ROOT CANAL

(76) Inventor: Yoshitsugu Terauchi, 3-2, Chuo-rinkan 3-chome, Yamato-shi, Kanagawa (JP)

( * ) Notice: Subject to any disclaimer, the term of this patent is extended or adjusted under 35 U.S.C. 154(b) by 254 days.

(21) Appl. No.: 10/245,527

(22) Filed: Sep. 17, 2002

(65) Prior Publication Data
US 2003/0124485 A1 Jul. 3, 2003

(30) Foreign Application Priority Data
Sep. 21, 2001 (JP) .............................. 2001-289852

(51) Int. Cl.
*A61C 5/02* (2006.01)
*A61C 3/00* (2006.01)

(52) U.S. Cl. ...................................... 433/224; 433/141

(58) Field of Classification Search ................ 433/102, 433/165, 224, 141, 163; 606/113
See application file for complete search history.

(56) References Cited

U.S. PATENT DOCUMENTS

| 1,461,865 | A | * | 7/1923 | Day ............................ 606/113 |
| 1,606,497 | A | * | 11/1926 | Berger ........................ 606/113 |
| 3,181,533 | A | * | 5/1965 | Heath ......................... 606/113 |
| 4,247,285 | A | * | 1/1981 | Roig-Greene ............... 433/141 |
| 4,746,292 | A | * | 5/1988 | Johnson ...................... 433/141 |
| 4,909,789 | A |   | 3/1990 | Taguchi et al. |
| 5,201,741 | A | * | 4/1993 | Dulebohn .................... 606/113 |
| 5,207,686 | A | * | 5/1993 | Dolgin ........................ 606/113 |
| 5,755,573 | A | * | 5/1998 | LeBlanc ...................... 433/159 |
| 5,788,710 | A | * | 8/1998 | Bates et al. .................. 606/113 |
| 5,792,148 | A | * | 8/1998 | Laxvik ........................ 606/131 |
| 5,868,570 | A | * | 2/1999 | Hickok et al. ............... 433/102 |
| 5,879,160 | A | * | 3/1999 | Ruddle ........................ 433/141 |
| 6,227,855 | B1 | * | 5/2001 | Hickok et al. ............... 433/141 |

FOREIGN PATENT DOCUMENTS

JP 62-286454 12/1987

* cited by examiner

*Primary Examiner*—Cary E. O'Connor
(74) *Attorney, Agent, or Firm*—Harness, Dickey & Pierce, P.L.C.

(57) ABSTRACT

This invention provides a device for removing a broken piece left in the root canal of a tooth comprising a handle to be held by the operator, a portion for fastening the broken piece, and a trigger component for operating the fastening portion.

3 Claims, 9 Drawing Sheets

(a)

(b)

(a)

(b)

(c)

(a)

(b)

(a)            (b)

(a)

(b)

(a)

(b)

(c)

DEVICE FOR REMOVING A BROKEN INSTRUMENT, ASSISTING INSTRUMENTS, AND THE METHOD TO RETRIEVE A BROKEN INSTRUMENT FROM THE ROOT CANAL

BACKGROUND OF THE INVENTION

1. Field of the Invention

The present invention relates to a device for removing a broken piece of an instrument left in the root canal of a tooth, its supportive instruments, and a method for removing such a broken piece using them.

2. Description of the Related Art

The hard tissue of a tooth is corroded by lactic acid which bacteria produce by digesting food remains in the oral cavity and results in dental caries. In the dental treatment, when the lesion involves the dental pulp, root canal therapy is performed, in which the content of the pulp is removed, the root canal communicating with the pulp is enlarged as needed, the operated tissues is sterilized, and the resulting cavity is filled with an inert material such as gattapercha.

It is easily anticipated that instruments for treatment such as files etc. which are used for enlargement of the root canal in root canal therapy will be contaminated with debris, bacteria, etc. in removing dentin, cement and pulp etc.

It is ideal, therefore, to use disposable instruments for every new patient to be treated. In practice, however, the dentist usually repeats washing and sterilizing instruments every time after use, and keeps using until they turn out to no longer endure further use functionally.

In the later phase of its life after the repeated use for a long time, it occurs not infrequently that the tip of the instruments is broken off during treatment. Once the resulting piece is left in the root canal of a treated tooth, it is difficult to deal with the problem or remove the piece, and thus the piece often is left there.

SUMMARY OF THE INVENTION

The present invention provides a device for removing a broken piece left in the root canal of a tooth comprising a handle to be held by an operator, a fastening portion for fastening the broken piece, and operating means for operating the fastening portion.

The other features of the present invention will be apparent by the description of the present specification with reference to the attached figures.

BRIEF DESCRIPTION OF THE DRAWINGS

FIGS. 2a and 2b illustrate the device when it is non-operating and operating, respectively.

DESCRIPTION OF THE PREFERRED EMBODIMENTS

Figure 1:
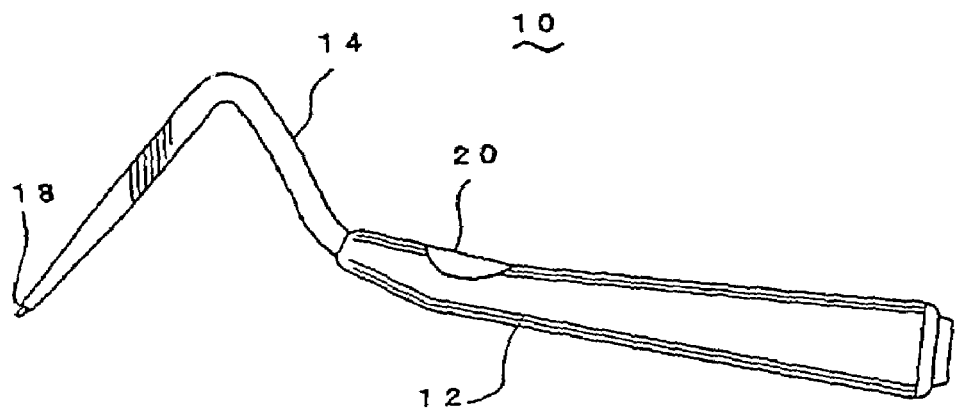
FIG. 1 is an overview of a removing device representing the first embodiment of this invention.

Reading the description of this specification with reference to the attached drawings will reveal at least the followings.

One embodiment of the present invention is directed to a device for removing a broken piece that enables secure removal of the broken piece from the root canal of a tooth by simple operations. The device is for removing a broken piece of an instrument left in the root canal of an operated tooth, and comprises a handle to be held, a fastening portion for fastening the broken piece, and operating means for operating the fastening portion.

In another embodiment of the present invention, the device further comprises a guide tube that protrudes at the distal end of the handle and the distal end thereof contains the fastening portion.

In yet another embodiment of the present invention, the guide tube has a blind distal end that has a pair of small throughholes; and the fastening portion comprises a wire that forms a loop at the distal end of the guide tube by passing through the pair of throughholes.

In yet another embodiment of the present invention, the guide tube has a blind distal end which has a small throughhole; and the fastening portion comprises a wire that forms a loop at the distal end of the guide tube by passing through the small throughhole and being fixed on the distal end of the guide tube.

In yet another embodiment of the present invention the fastening portion fastens the broken piece of the instrument, by pulling the wire in the guide tube backward by means of the operating means, thereby constricting the loop formed with the wire.

In yet another embodiment of the present invention, operating of the operating means gives a tensile force to the wire, which is pulled into the guide tube.

In yet another embodiment of the present invention, operating of the operating means slides a connection point of the wire, which is pulled into the guide tube.

In yet another embodiment of the present invention, a rod is slidably inserted into the handle and at least one end of the wire is connected to the rod.

In yet another embodiment of the present invention, an device for removing a broken piece is for removing a broken piece left in the root canal of a tooth and comprises a handle to be held by an operator, a guide tube protruding at the distal end of the handle, a wire whose two legs are passed through the interior of the guide tube and the handle so that their ends are fixed at the proximal end of the handle, a fastening portion provided at the protruding end from the distal end of the guide tube and operating means installed in a part of the handle, and with a broken piece surrounded with the fastening portion, the operating means are operated so as to pull the wire legs backward, thereby drawing the fastening portion towards the distal end of the guide tube, and restraining the broken piece inside the fastening portion.

Yet another embodiment of the present invention is directed to providing a supportive instrument that can expose the head of a broken piece left in the root canal of a tooth to such an extent as to enable the device to hold the head of the piece. The supportive instrument comprises a handle to be held, and a forked portion for cutting, having a fork end with each end comprising an inner sloping portion and an outer sloping portion.

In yet another embodiment of the present invention, the inner sloping portion described above has a cutting edge.

A supportive instrument according to yet another embodiment of the present invention is for supporting the removal of a broken piece of an instrument left in the root canal of a tooth and comprises a handle to be held, an arc-shaped cutting edge for cutting off dentine and ultrasonic vibration generator for applying an ultrasonic vibration to the cutting edge.

In yet another embodiment of the present invention, the supportive instrument further comprises a metal sleeve whose proximal end is freely attached to and detached from the distal end of the handle and whose distal end contains the cutting edge.

Yet another embodiment of the present invention is directed to providing a method for efficiently removing a broken piece of an instrument from the root canal of a tooth using these instruments and/or other dental instruments. This method for removing a broken piece is for removing it from the root canal of a tooth and comprises the steps of. fastening the broken piece-at a fastening portion provided at the distal end of a device for removing a broken piece of the instrument and withdrawing the device with the broken piece fastened.

In yet another embodiment of the present invention, the method further comprises a step of cutting off the dentine surrounding the head of the broken piece in the root canal of a tooth using a supportive instrument, thereby exposing the head.

In yet another embodiment of the present invention, the method further comprises a step of cutting off the dentine surrounding the head of the broken piece in the root canal of a tooth using a supportive instrument equipped with an ultrasonic vibration generator, thereby exposing the head.

Figure 2:
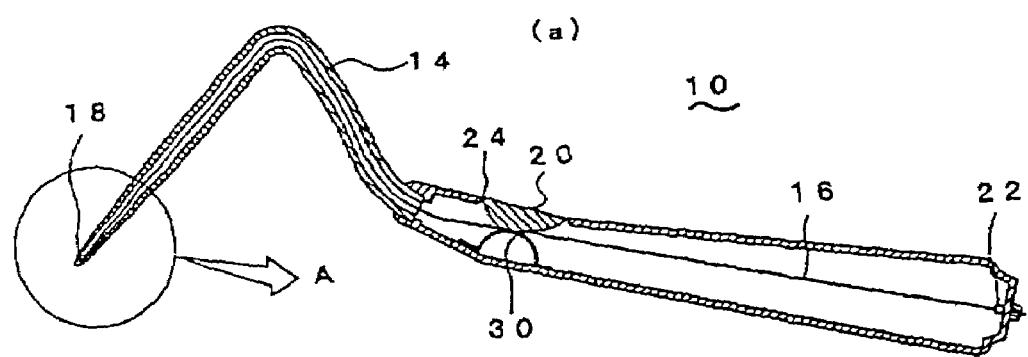
FIG. 2 shows sectional views of the same device.
Figure 2:
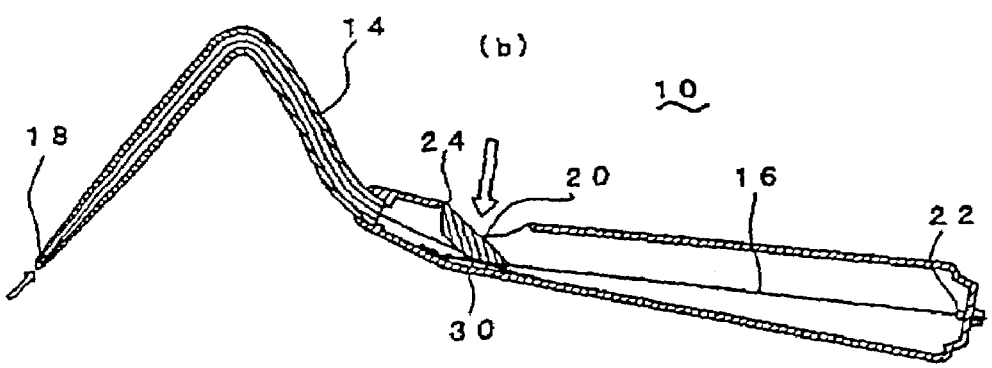
Figure 3:
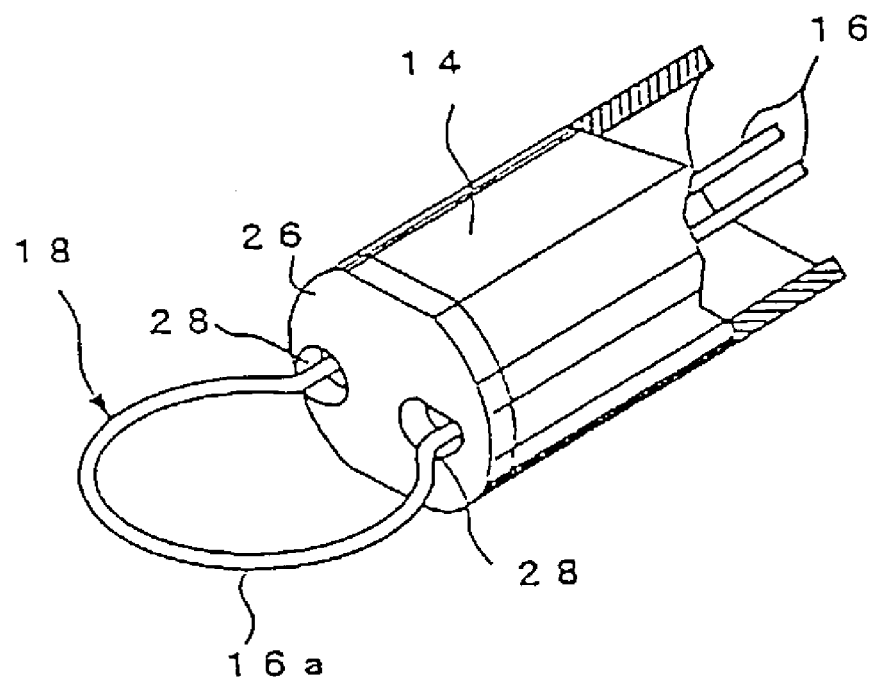
FIG. 3 shows magnified views of the part designated as A in FIG. 2.
Figure 3:
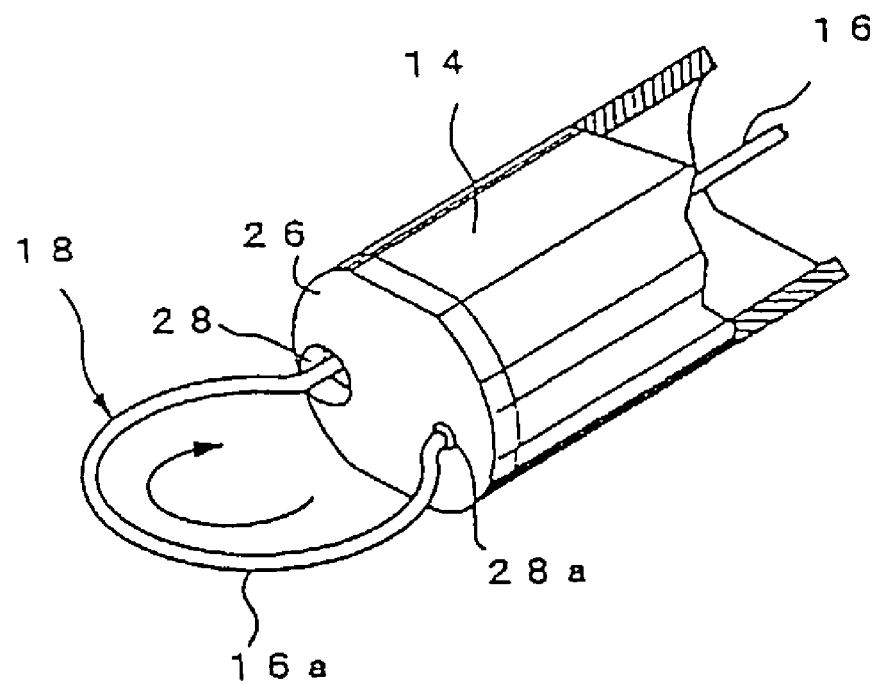

The preferred embodiments of the present invention will be detailed below with reference to the attached drawings. FIGS. 1 to 3 illustrates a removing device representing the first embodiment of the present invention.

The instrument 10 are provided with a handle 12 to be held by the operator, a guide tube 14 protruding from the distal end of the handle 12, a wire 16 passing through in the handle 12 and the guide tube 14, a fastening portion 18 formed at the protruding portion of the wire 16 from the tip end of the guide tube 14, and a trigger button 20 provided at the disto-lateral side of the handle 12.

The handle 12 is hollow, is made from a material that ensures a size and a shape allowing easy hand gripping and handling and permits easy sterilization, like common dental instruments. A wire adjuster 22 is provided inside the proximal end of the handle 12 and combine the ends of the wire 16 passing through in the handle 12 so as to be able to adjust its length and tension.

The guide tube 14 is a tapered metal sleeve made from nickel, titanium, an alloy, stainless steel, a cobalt chromium alloy, etc. with a diameter of about 0.4 mm and a length of about 38 mm and may be prepared by modifying a syringe for washing the root canal.

The guide tube 14 is curved from its proximal end joining to the handle 12 to its distal end so as to allow the distal end of the tube to be easily introduced into the oral cavity over the dental arch. Needless to say, other types of curved shape may take than this type of curved shape, considering the difficulty to be introduced according to a site operated.

The distal end of the guide tube 14 is closed with a stopper 26 as shown in the magnified view of the distal end of FIG. 3a. The blind terminal end has a pair of small throughholes 28 for receiving the wire.

The wire 16 is a single strong wire of stainless steel plated with nickel on its outer surface with a diameter of about 0.06 mm. As shown in FIG. 3, both ends of the wire are passed through the respective small throughholes 28, introduced into the guide tube 14 and the handle 12, and connected with the wire adjuster 22 so that the wire forms a loop 16a outside the distal end of the guide tube 14 and provide a fastening portion 18 comprising a closed space surrounded by the loop 16a and the stopper 26. Alternatively, as shown in the magnified view of FIG. 3b, the guide tube 14 may be formed so that one end of the wire 16 running through the guide tube 14 passes through the small throughhole 28 formed on the stopper 26, forms a loop outside the stopper and is fixed to a fixing site 28a on the stopper 26.

A trigger button 20 has an outer surface that is flush with that of the handle 12, and an inner surface bulged towards the hollow cavity of the handle 12. This trigger button 20 is closely fitted to a slender slot formed on a disto-lateral region of the handle 12, and is hinged to a trigger holder 24 provided at the distal side of the slot 12a.

The bulged surface of the trigger button 20 contacts with the outer surface of the wire 16 and with a spring 30 attached to the inner wall of the handle 12. When the trigger button 20 is not operated, as shown in FIG. 2a, its outer surface is flush with the outer surface of the handle. When the trigger button 20 is pressed, as shown in FIG. 2b, depressing the spring 30, it moves inward with the trigger holder 24 as a pivot, and presses and moves the wire so as to constrict the loop 16a of the fastening portion 18.

When the trigger button 20 is released, it returns to the original position, while the loop 16a of the wire 16 remains to be in contact with the distal end surface of the stopper 26. Therefore, to restore the original shape of the loop, it is necessary to insert a thin stick such as a needle between the loop 16a, and the stopper 26, and to squeeze the stick to widen the loop 16a, and thus it is possible to allow the loop to freely take any size, shape, tilting, etc. Even if an operation turns out to be a failure, the device may be used repeatedly until the wire is broken.

Figure 4:
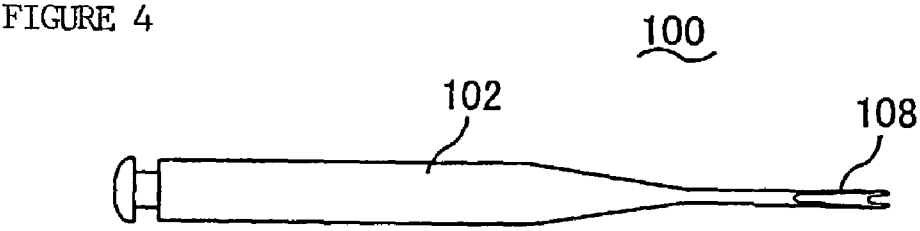
FIG. 4 illustrates a stainless steel bar also representing the first embodiment.
Figure 4:
Figure 4:
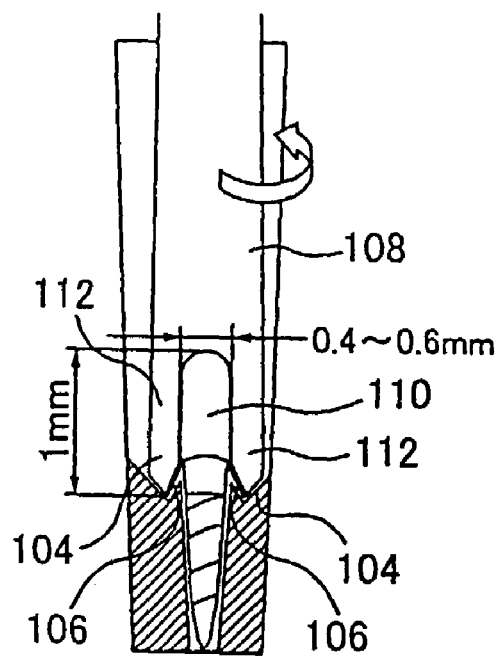
Figure 5:
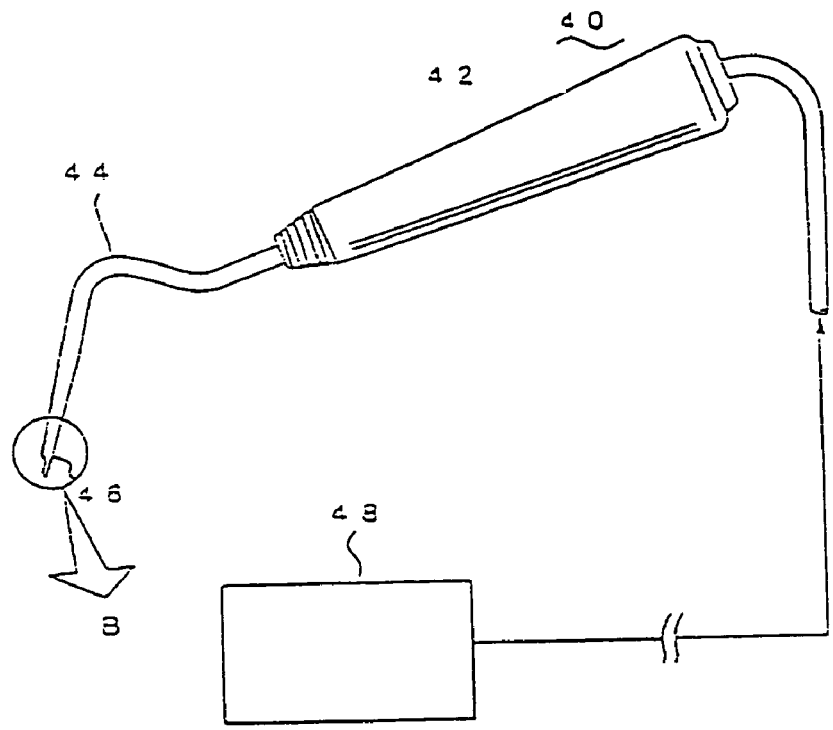
FIG. 5 illustrates a supportive instrument connected to an ultrasonic vibration generator representing the first embodiment.
Figure 6:
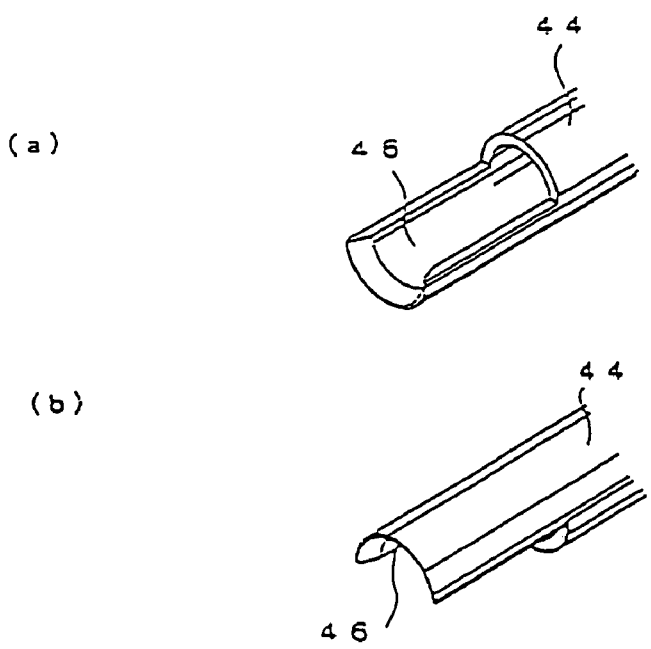
FIGS. 6a and 6b are magnified views of the part designated as B in FIG. 5.

The composition of the supportive instruments will be described with reference to FIGS. 4, 5 and 6.

The supportive instrument is used when a broken piece of a file is entrapped in the root canal of a tooth and its head is visible, or when a broken piece is entrapped in the root canal of a tooth but is not directly recognized by vision nor with a microscope and expose the head of the broken piece from the root canal and enable the operation for removing it by the removing device 10 described above by cutting the dentine near the top of the broken piece toward the broken piece.

The first supportive instrument is a stainless steel bar 100 with an overall length of about 3 cm. This is used for exposing about 1 mm of the head of the broken piece. The bar comprises a handle 102 to be held by an operator and a forked portion 108 with forked cutting ends, each of which comprises an outer sloping portion 104 and an inner sloping portion 106.

The handle 102 has a cylindrical shape with a cross-section of about 0.5 cm in diameter so that it is easily rotated by one hand. The handle has a tapered distal end that continues into a flattened wide cutting portion 108.

The bar 100 has a fork end at the cutting portion 108 and thus the cutting portion 108 is totally U-shaped. The recess 110 of the U-shaped portion has a depth of 1 mm and a width of about 0.5 mm. Each protrusion of the U-shaped portion has a width of about 0.5 cm. Each protrusion has, on its distal end, an outer sloping portion 104 and an inner sloping portion 106 that has a cutting edge. The inner sloping portion 106 provided with the cutting edge cuts the dentine surrounding the head of a broken piece of a file. The outer sloping portion 104 is not provided with a cutting edge to avoid the useless cut of dentine around the head of a broken piece of a file.

Next, the second supportive instrument 40 comprises a handle 42 to be held by an operator; a slender metal sleeve 44 which is freely attached to and detached from the distal end of the handle 42 and which is able to be freely deformed; a shovel-shaped cutter 46 which is obtained by chipping a half distal end of the metal sleeve 44 and sharpening the distal end of the remaining half end; and an ultrasonic vibration generator 48 that is connected to the posterior end of the handle 42. The metal sleeve 44 is to be worn, and must be replaced with a new one when it is broken, cracked or worn, and its linear shape is freely altered to meet a symptom.

The proximal end of the handle 42 is connected to the ultrasonic vibration generator 48. The ultrasonic vibration-generating treatment machine such as an ultrasonic scaler may be used as the ultrasonic vibration generator 48.

The metal sleeve 44 has a diameter as large as a needle, and multiple kinds with different diameters ranging from 0.3 to 1.0 mm are prepared. As they have a certain life span for use, it is composed to be readily replaced with a new one from the distal end of the handle.

As shown in FIG. 6*a*, two types of the cutting edge are prepared according to the direction of the arc of its cutting edge with respect to the handle: upward and downward. This is because the handle 42 is so large that it is practically impossible to rotate the handle 42 in the oral cavity. Similarly, two other kinds with different directions may be prepared: rightward and leftward. All of the cutting edge 46 are hardened and sufficiently sharpened.

Figure 7:
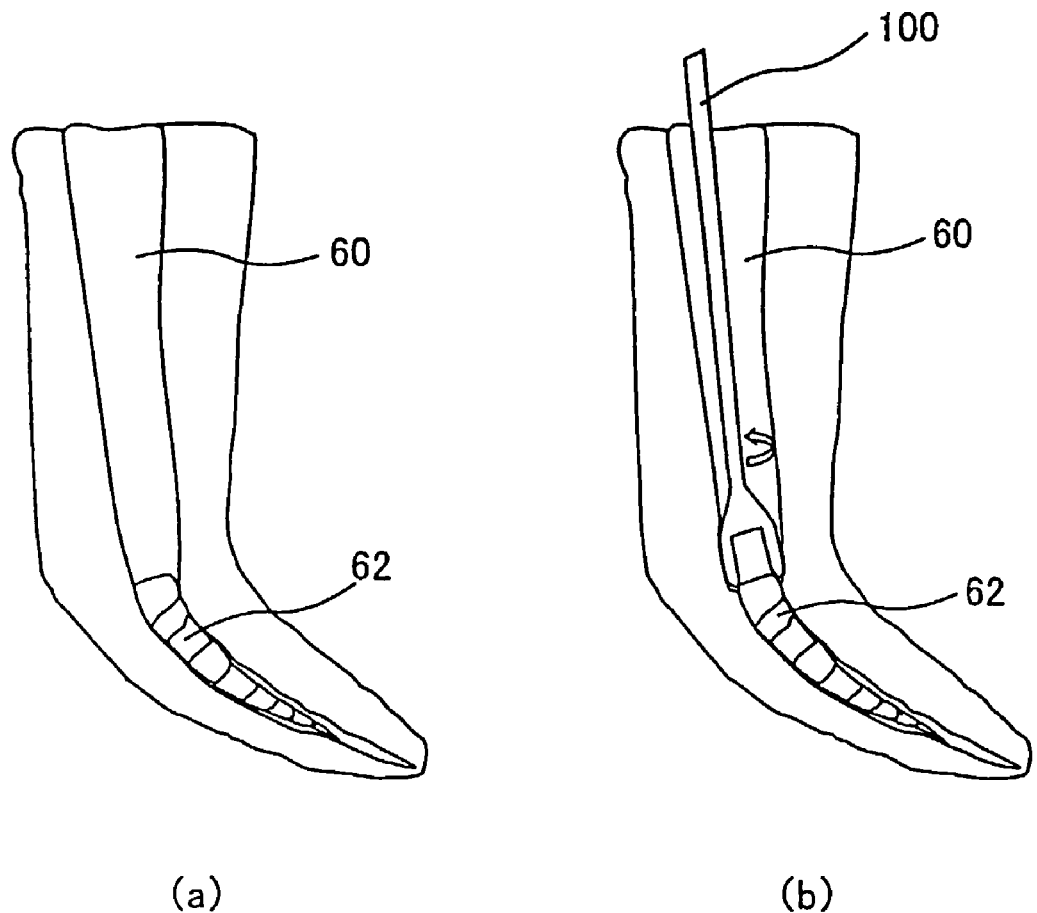
FIG. 7 illustrates how the stainless steel bar representing the first embodiment is operated.
Figure 8:
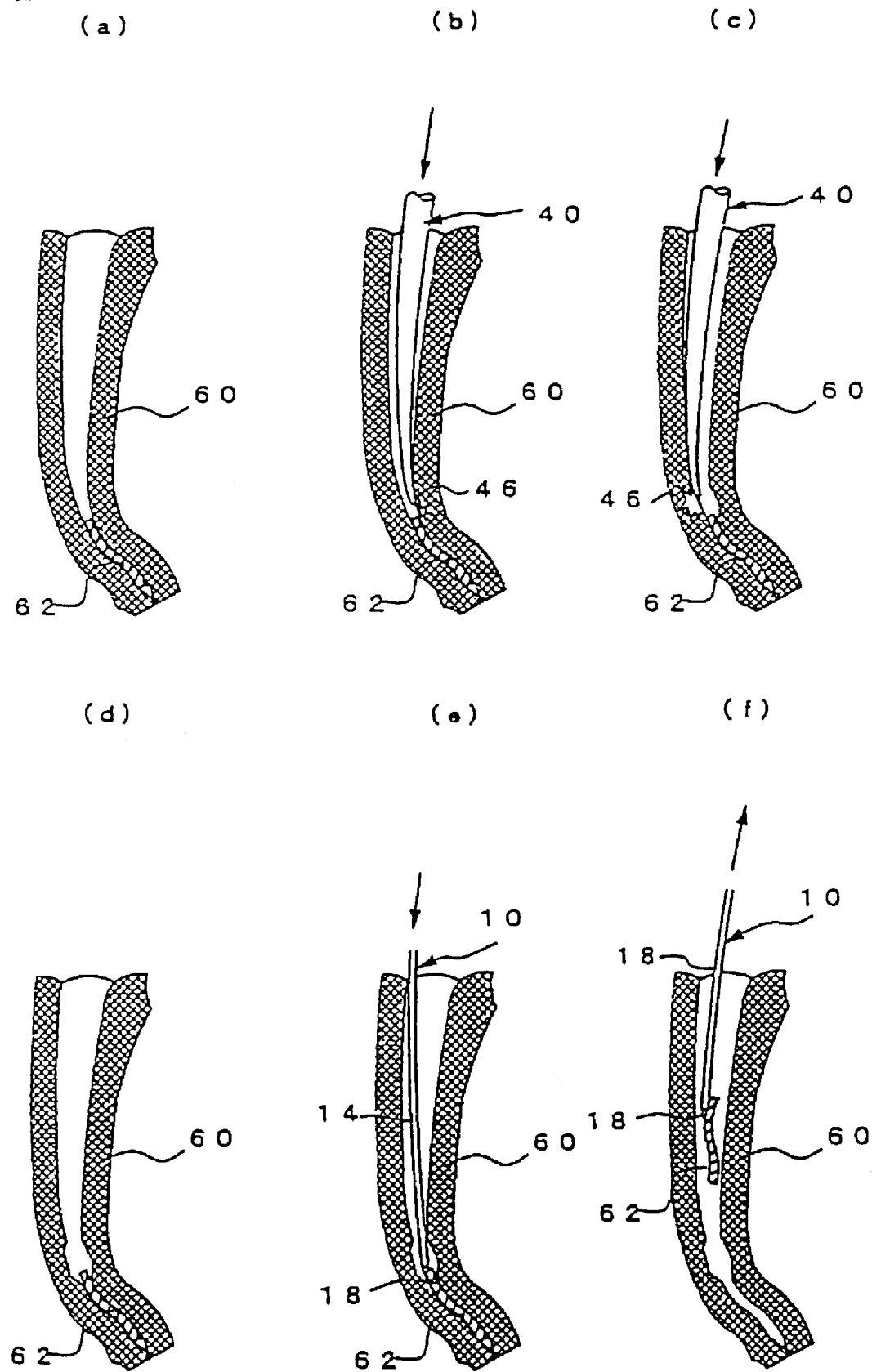
FIG. 8 illustrates the cross-sections to show the supportive instrument with an ultrasonic vibration generator and the procedure for removal of a broken piece by use of the removing device representing the first embodiment.

The procedure of removing a broken piece of an instrument from the root canal of a tooth using the above-described removing device 10 in combination with the supportive instruments 40, 100 will be described with reference to FIGS. 7 and 8.

It should be noted that, a broken piece in the root canal of a tooth is confirmed by, for example, taking an X-ray photo in advance, and then the removal operation proceeds while the root canal is observed under a dental microscope.

The microscope is a dental stereo-microscope. An operator may operate, observing directly an image enlarged through the object lens in the root canal illuminated by a halogen or xenon lamp incorporated in the microscope by peeping into the eye lenses with both eyes, or observing an image through a CCD camera on a monitor. The image of the root canal is magnified 4 to 25 fold and the operator may operate, selecting an appropriate magnification for the operation. Since it is often difficult for the operator to vertically direct the object lens towards the root canal, the operator holds a dental mirror with a hand and focuses the object lens onto the image on the mirror in many cases. However, when it is hard to stabilize the mirror only by one hand, a mirror fixation instrument can be provided between the mirror and the rubber dam clamp used for root canal therapy. The mirror fixation instrument comprises a clamp portion for clamping the body of a mirror and a part of the bow of the rubber dam clamp and a ball joint that combines clamp portions at its both ends and allows it to make a 360° turn. The clamp portion can be freely attached to a mirror and a rubber dam clamp through a simple spring action. Thus, the image of the root canal reflected on the mirror will become stable.

In many clinical cases, as shown in a cross-sectional view of FIG. 7*a*, a broken piece 62 of a file sticking into a thinner portion of the root canal 60 of a tooth exposes its head.

To minimize the abrasion of dentine around the head of the broken piece when the ultrasonic vibration-based supporter instrument 40 is used, the dentine around the head of the broken piece is cut in advance with another supporter instrument, the stainless steel bar 100, which makes the use of the ultrasonic vibration-based supporter instrument 40 easier.

First, the bar 100 is positioned so as to allow its forked cutting portion 108 of the distal end of the bar 100 to entrap the head of a broken piece of a file within its recess 110. The bar 100 is then rotated opposite to the turn direction of the thread inscribed on the broken piece. During this operation, the cutting edge on the inner sloping portion 106 of the cutting portion 108 cuts dentine close to the string head, while the outer sloping portion have no cutting edge, which prevents the surrounding dentine from being cut uselessly. When the bar 100 is rotated opposite to the turn direction of the thread inscribed on the broken piece, the string head 62 may also be rotated in the same direction, and it is expected that the string head 62 will be more or less extracted therewith from the canal 60.

After the dentine around the broken piece 62 was dug about 1 mm, the ultrasonic vibration-based instrument 40 is used to further cut the dentine around the broken piece 62. In this case, between two kinds of the supporter instrument 40 prepared, the one in which its metal sleeve 44 has a cutting edge 46 facing downward is brought into contact with one half of the dentine wall around the head of the broken piece 62, as shown in FIG. 8*b*, and ultrasonic vibration is applied, thereby cutting one side of the dentine around the head of the broken piece 62. Next, the metal sleeve having the downward facing cutter is used and is brought into contact with the other half of the dentine wall around the broken piece, as shown in FIG. 8*c*, and ultrasonic vibration is applied, thereby cutting the other side of the dentine around the head of the broken piece 62.

The steps FIG. 8*b* and FIG. 8*c* may be reversed. The cutting procedure may also become possible if the operation of the handle 42 is performed outside the oral cavity and the cutting edge is put on the aimed site, taking advantage of the curving of the metal sleeve 44.

When about 1.0 to 1.5 mm of the head of the broken piece is exposed through the above-described procedure, as shown in FIG. 8*d*, the site to be held become secured and the use of the removing device 10 become possible.

If the root canal is curved too much, in order to secure the visibility, the removing procedure needs to be done gradually from the upper root canal 60 so as to get an unobstructed view.

In any case, because it is the delicate removing operation in narrow places, utmost care must be taken.

The steps as shown in FIG. 8b to FIG. 8d may be omitted when the head of the broken piece of the file 62 is exposed so much as to be hold for the operation.

Next, as shown in FIG. 8e, the guide tube 14 of the removing device 10 is inserted into the root canal 60, the loop 16a of the fastening portion 18 is placed around the head of the broken file 62, and the trigger button 20 is operated to constrict the loop 16a, thereby fastening the head of the broken file 62.

Keeping this state of the removing device 10 as it is, it is withdrawn, as shown in FIG. 8f, if necessary, with being rotated or swung, thereby being able to remove the broken piece of the file 62.

After the removal, the place can be applied by general dental treatment such as sterilization, cleaning, and root canal therapy.

In the first embodiment described above, the two supportive instruments 100, 40 are used for pretreatment. However, it is not necessary to use both of the two instruments depending on the state of the broken piece of the file 62 and in such a case, after cutting the dentine around the site with either one, the removing device 10 can be used. Alternatively, in the situation that the removing device 10 can be used without supporting instruments 100, 40, they do not need to be used.

Figure 9:
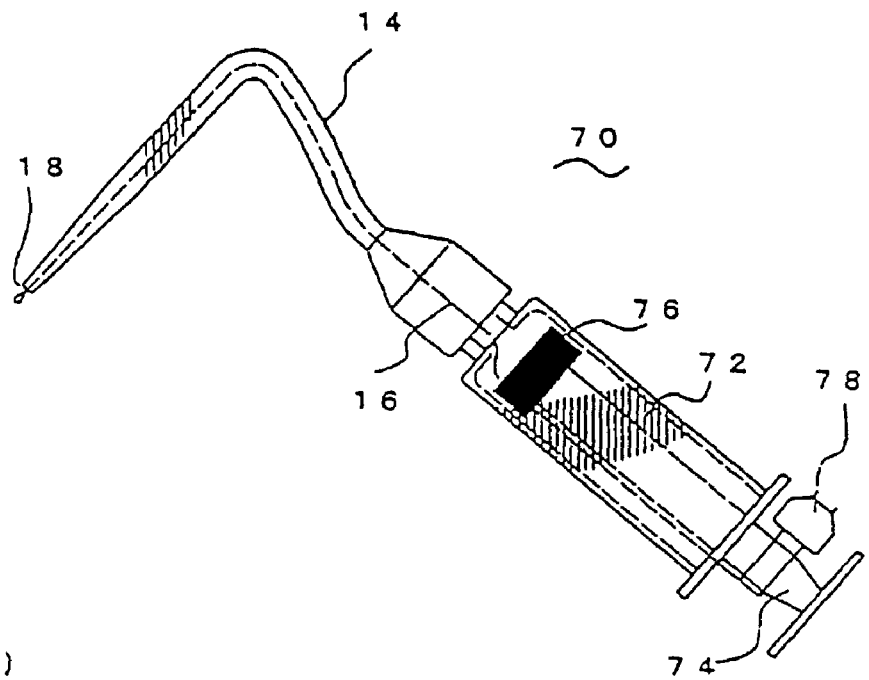
FIGS. 9a and 9b illustrate the removing device representing the second embodiment of this invention when a fastening portion is non-operating and operating, respectively.
Figure 9:
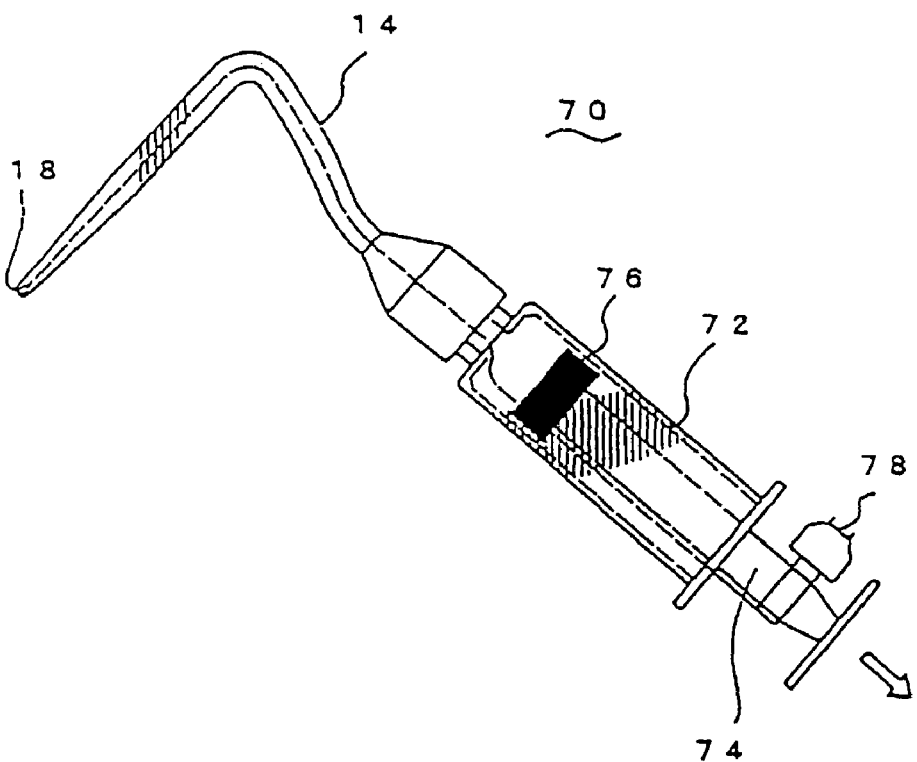

FIG. 9 shows the second embodiment of the removing instrument. The instrument 70 shown in the figure use, for example, a 25 ul micro-syringe 72 and a plunger (rod) 74 which is slidably equipped to the posterior part of the syringe 72 as the handle and operating means and the guide tube 14 adapted by a root canal washing needle is provided at the distal end of the syringe 72 as described above. A wire 16 forms a loop at the distal end of the guide tube 14 that serves as a fastening portion 18 between the distal end of the guide tube 14 and the wire 16.

The ends of the wire 16 is passing through in the guide tube 14, the micro-syringe 72, and the piston 76 attached to the distal end of the plunger 74, exit from the posterior end of the syringe 72, and are fastened to an adjuster block 78 mounted to the posterior region of the plunger 74 in such a manner as to permit the adjustment of the wire length.

Therefore, in the non-operating situation, the plunger 74 is pushed in as shown in FIG. 9a, while in the operating situation, when the plunger 74 is withdrawn to the posterior, the wire 16 is pulled in, the fastening portion 18 is constricted, and thus the broken piece of the file is fastened.

With this embodiment, it is possible to pull in the wire 16 by a larger distance by extracting the plunger 74, and thus it become possible to fasten the broken piece of the file more firmly.

The procedure necessary for removing a broken piece of the file using the supportive instrument 40 and the removing instrument 70 are the same with those shown above in FIG. 8, and thus explanation thereof will be omitted.

FIGS. 10a and 10b show the third embodiment of the removing device. With the removing device 80 shown in the figure, the trigger button 20 of the first embodiment is replaced with slidable operating means. Specifically, a slide trigger 82, comprising an elongated slidable portion 82a on the handle 12 to be held, a stopper portion 82b which is integrated with the proximal end of the slidable elongated portion 82a and covers the proximal end of the handle 12 (the inset figure of FIG. 10a shows a flat view of the proximal end of the stopper portion), and a projection 82c attached to the distal end of the elongated slidable portion 82a, is securely provided via a ring 83. The posterior ends of the wire 16 that are passing through in the handle 12 are fastened via a wire adjuster 22 to the stopper portion 82b.

Figure 11:
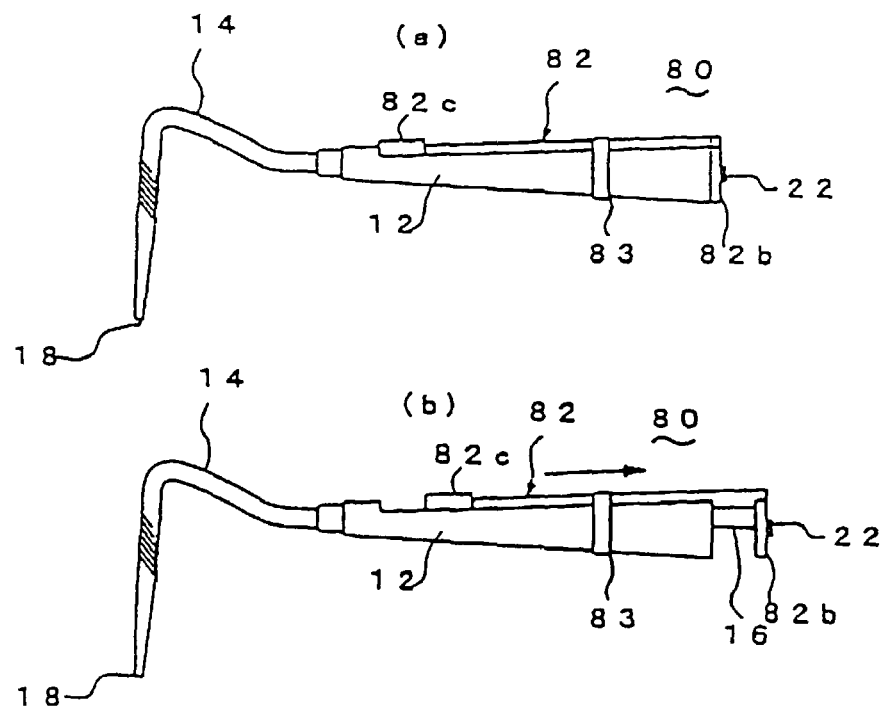
FIGS. 11a and 11b illustrates the removing device when it is non-operating and operating, respectively.

If, in the situation as shown in FIG. 11a, the operator holds the handle 12, put a finger on the projection 82c and slide it back, the slide trigger 82 totally move backward, the wire 16 that are attached via the wire adjuster 22 to the stopper portion 82b are also pulled backward, the loop 16a is constricted at the fastening portion 18, securely hold the broken piece, and get the same effects as the embodiments described above.

Figure 12:
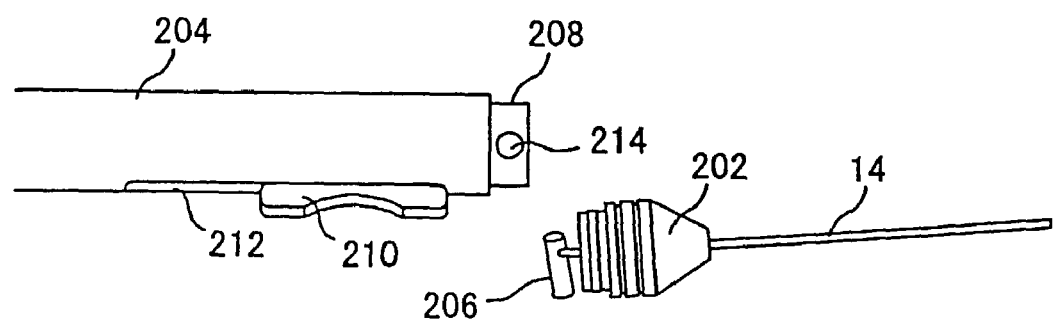
FIGS. 12a, 12b and 12c illustrate a removing device representing the fourth embodiment of this invention.
Figure 12:
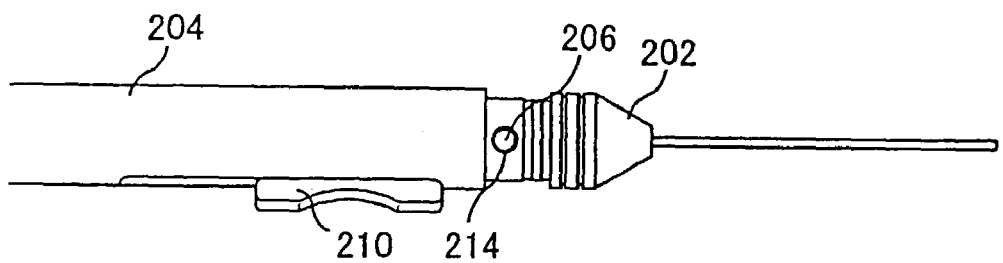
Figure 12:
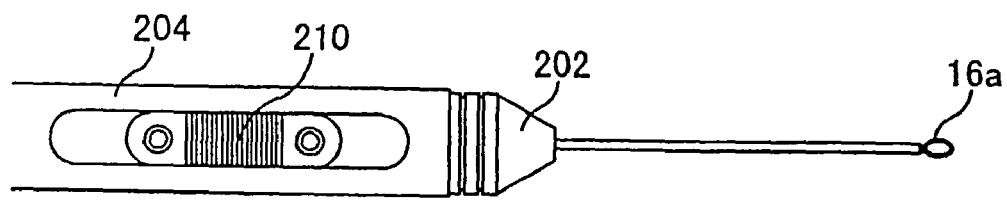

FIGS. 12a and 12b show the fourth embodiment of the removing device. The fourth embodiment of the removing device 80 comprises a tip portion 202 and handle 204 that can be separated from each other as shown in FIG. 12a. A guide tube 14 provided at the tip portion 202 is linear, with a diameter of 27G and a length of 30 mm. A wire 16 that forms the fastening portion 18 at the distal end of the guide tube 14 as in the first embodiment is connected to columnar metal connector 206 at the posterior of the tip portion 202.

The aluminum-made handle 204 is hollow in which an inner cylinder 208 is inserted. A slide trigger 210 is provided at the lateral surface of the inner cylinder 208, and protrudes outside through a slit 212 formed on the lateral wall of the handle 204. When the slide trigger 210 is moved to the most distal position, the head of the inner cylinder 208 slightly protrudes from the distal end of the handle 204 as shown in FIG. 12a. When the slide trigger 210 is pulled in a proximal direction along the slit 212, the inner cylinder 208 moves in the proximal direction in association, so that the head of the inner cylinder is hidden in the handle 204 (not illustrated).

The head of the inner cylinder 208 has a transverse throughhole 214, like a tunnel, to which the metal connector 206 can be closely fitted, and the metal connector 206 can be inserted into the throughhole 214 as shown in FIG. 12b. The tip portion 202 is attached to the handle 204 in this situation to form a removing device 80 as shown in FIG. 12c. If the slide trigger 210 is moved backward, the wire 16 in the tip portion 202 is pulled backward and the loop 16a of the wire 16 at the fastening portion 18 is constricted. Thus, in the fourth embodiment, when a broken piece of a file exists, it can be constricted and ensures the same effects as are obtainable from the embodiments described earlier.

It should be understood that other variants and modifications not mentioned in the embodiments are also included in this invention, as far as they remove an broken piece, by placing a loop around the head of a fragment, and then constricting the loop via remote operation, thereby holding firmly the head of the fragment within its circle for subsequent recovery.

Figure 10:
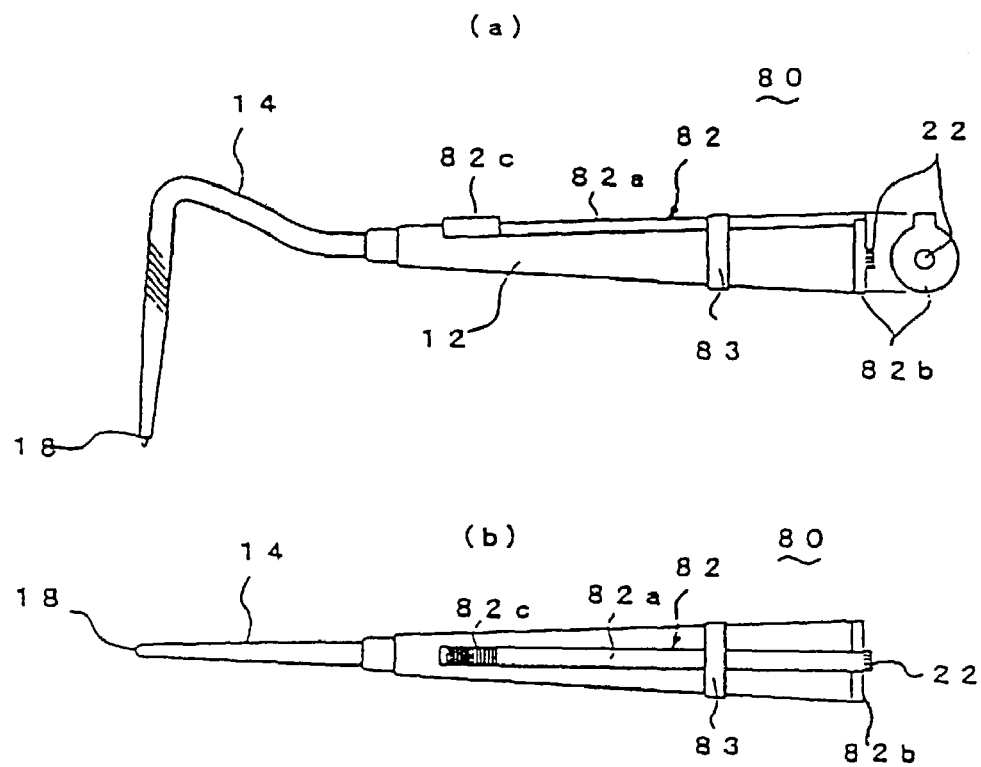
FIGS. 10a and 10b are lateral and top views of a removing device, respectively, representing the third embodiment of this invention.

REFERENCE NUMERALS IN THE FIGURES 10, 70: Broken piece removing instrument; 12: Handle; 14: Guide tube; 16: Wire; 16a: Loop; 18: Fastening portion; 20: Trigger button; 24: Stopper; 26: SamII hole; 40: Supportive instrument; 42: Handle; 44: Metal Sleeve; 46: Cutting edge; 48: Ultrasonic vibration generator; 60: Root canal; 62: Broken piece; 72: Micro-syringe (holder); 74: Plunger (operating means); 100: Stainless steel bar; 102: Handle; 104: Outer sloping portion; 106: Inner sloping portion; 108: Cutting portion; 110: Recess; 112: Projection;

202: Tip portion; 204: Handle; 206: Connecting element; 208: inner cylinder; 210: Slide TriGGer; 212: Slit; 214: Throughhole Cutting portion; 110: Recess; 112: Projection; 202: Tip portion; 204: Body; 206: Connecting element; 208: Inner cylinder; 210: Handle; 212: Slit; 214: Throughhole

What is claimed is:

1. A method for removing a broken piece of an instrument left in the root canal of a tooth comprising the steps of:
    moving a trigger component to activate operating means;
    fastening the broken piece at a fastening portion provided at the distal end of a device for removing the broken piece of the instrument; and
    withdrawing said device with the broken piece fastened.

2. A method for removing a broken piece as set forth in claim 1 comprising the step of:
    cutting off dentine surrounding the head of the broken piece in the root canal of a tooth using a supportive instrument, thereby exposing the head.

3. A method for removing a broken piece as set forth in claim 1 or 2 further comprising the step of:
    shaving off the dentine surrounding the head of the broken piece in the root canal of a tooth using a supportive instrument equipped with an ultrasonic vibration generator, thereby exposing the head.

* * * * *